United States Patent
Miller et al.

(10) Patent No.: US 7,766,049 B2
(45) Date of Patent: *Aug. 3, 2010

(54) BALLOON CATHETER

(75) Inventors: John Miller, Redwood City, CA (US);
Martin Dieck, Cupertino, CA (US);
Maria Aboytes, East Palo Alto, CA (US); Ryan K. Pierce, Mountain View, CA (US)

(73) Assignee: Concentric Medical, Inc., Mountain View, CA (US)

( * ) Notice: Subject to any disclaimer, the term of this patent is extended or adjusted under 35 U.S.C. 154(b) by 1080 days.

This patent is subject to a terminal disclaimer.

(21) Appl. No.: 10/692,424

(22) Filed: Oct. 22, 2003

(65) Prior Publication Data
US 2004/0079429 A1 Apr. 29, 2004

Related U.S. Application Data

(63) Continuation of application No. 10/085,589, filed on Feb. 28, 2002, now Pat. No. 6,638,245, which is a continuation-in-part of application No. 09/892,349, filed on Jun. 26, 2001, now Pat. No. 6,702,782.

(51) Int. Cl.
*F16L 11/00* (2006.01)
(52) U.S. Cl. .................. 138/116; 138/125; 138/132; 606/194; 604/96.01; 604/97.01; 604/164.1; 604/523
(58) Field of Classification Search ............... 138/111, 138/116, 117, 123–125, 130, 132; 606/191, 606/194; 604/523, 96.01, 528, 93.01, 97.01, 604/99.01, 164.1, 164.13
See application file for complete search history.

(56) References Cited

U.S. PATENT DOCUMENTS

| 3,750,058 A | 7/1973 | Bankert, Jr. et al. |
| 4,105,022 A | 8/1978 | Antoshkiw et al. |
| 4,188,954 A | 2/1980 | Patel et al. |
| 4,259,960 A | 4/1981 | Taylor |
| 4,336,798 A | 6/1982 | Beran |

(Continued)

FOREIGN PATENT DOCUMENTS

WO    WO 89/11306    11/1989

(Continued)

OTHER PUBLICATIONS

Commedore, Temporary Occlusion Balloon Catheter, at <<http://www.cordis.com/Commodore_Balloon.cfm>>, visited on Jan. 1, 2002, 8 pgs. total.

(Continued)

*Primary Examiner*—James F Hook
(74) *Attorney, Agent, or Firm*—Townsend and Townsend and Crew LLP

(57) ABSTRACT

This is a balloon catheter having at least two lumens. One of the lumens is a large working lumen. The balloon catheter is especially useful as a guide catheter or micro catheter and may be used in a variety of therapeutic and diagnostic procedures. In particular, it has value in treating neurovascular embolic strokes in combination with other devices which are delivered to the stroke site through that working lumen. The remainder of the lumens typically are used to inflate and to deflate the balloon.

5 Claims, 9 Drawing Sheets

U.S. PATENT DOCUMENTS

| | | | |
|---|---|---|---|
| 4,484,586 A | 11/1984 | McMickle et al. | |
| 4,492,089 A | 1/1985 | Rohmer et al. | |
| 4,646,719 A | 3/1987 | Neuman et al. | |
| 4,886,496 A | 12/1989 | Conoscenti et al. | |
| 4,917,666 A | 4/1990 | Solar et al. | |
| 5,052,105 A * | 10/1991 | Mische et al. | 29/883 |
| 5,163,911 A | 11/1992 | Sirimanne et al. | |
| 5,195,972 A | 3/1993 | Inoue | |
| 5,253,653 A | 10/1993 | Daigle et al. | |
| 5,285,744 A | 2/1994 | Grantham et al. | |
| 5,295,994 A | 3/1994 | Bonutti | |
| 5,304,134 A | 4/1994 | Kraus et al. | |
| 5,304,198 A | 4/1994 | Samson | |
| 5,334,160 A | 8/1994 | Ellis | |
| 5,364,354 A | 11/1994 | Walker et al. | |
| 5,394,904 A * | 3/1995 | Winter et al. | 138/137 |
| 5,395,334 A | 3/1995 | Keith et al. | |
| 5,409,004 A | 4/1995 | Sloan | |
| 5,429,605 A | 7/1995 | Richling et al. | |
| 5,437,637 A | 8/1995 | Lieber et al. | |
| 5,453,094 A | 9/1995 | Metcalf et al. | |
| 5,484,412 A | 1/1996 | Pierpont | |
| 5,484,424 A * | 1/1996 | Cottenceau et al. | 604/525 |
| 5,492,532 A | 2/1996 | Ryan et al. | |
| 5,499,971 A | 3/1996 | Shapland et al. | |
| 5,501,668 A | 3/1996 | Kontos | |
| 5,512,051 A | 4/1996 | Wang et al. | |
| 5,527,292 A | 6/1996 | Adams et al. | |
| 5,552,818 A | 9/1996 | Agano et al. | |
| 5,562,725 A | 10/1996 | Schmitt et al. | |
| 5,571,161 A | 11/1996 | Starksen | |
| 5,573,508 A | 11/1996 | Thornton | |
| 5,606,981 A | 3/1997 | Tartacower et al. | |
| 5,620,649 A | 4/1997 | Trotta | |
| 5,628,754 A | 5/1997 | Shevlin et al. | |
| 5,649,909 A | 7/1997 | Cornelius | |
| 5,649,941 A | 7/1997 | Lary | |
| 5,653,691 A | 8/1997 | Rupp et al. | |
| 5,681,336 A | 10/1997 | Clement et al. | |
| 5,683,410 A | 11/1997 | Samson | |
| 5,695,008 A | 12/1997 | Bertet et al. | |
| 5,702,439 A | 12/1997 | Keith et al. | |
| 5,713,854 A | 2/1998 | Inderbitzen et al. | |
| 5,728,063 A | 3/1998 | Preissman et al. | |
| 5,733,301 A | 3/1998 | Forman | |
| 5,743,876 A | 4/1998 | Swanson | |
| 5,752,934 A | 5/1998 | Campbell et al. | |
| 5,755,690 A | 5/1998 | Saab | |
| 5,759,173 A | 6/1998 | Preissman et al. | |
| 5,769,817 A | 6/1998 | Burgmeier | |
| 5,772,631 A | 6/1998 | Lepor | |
| 5,776,099 A | 7/1998 | Tremulis | |
| 5,797,877 A | 8/1998 | Hamilton et al. | |
| 5,800,522 A | 9/1998 | Campbell et al. | |
| 5,810,767 A | 9/1998 | Klein | |
| 5,817,053 A | 10/1998 | Agarwal | |
| 5,823,995 A | 10/1998 | Fitzmaurice et al. | |
| 5,824,173 A | 10/1998 | Fontirroche et al. | |
| 5,827,201 A | 10/1998 | Samson et al. | |
| 5,827,231 A | 10/1998 | Harada | |
| 5,833,659 A | 11/1998 | Kranys | |
| 5,833,672 A | 11/1998 | Kawata et al. | |
| 5,836,892 A | 11/1998 | Lorenzo | |
| 5,836,912 A | 11/1998 | Kusleika | |
| 5,843,051 A | 12/1998 | Adams et al. | |
| 5,860,923 A | 1/1999 | Lenker et al. | |
| 5,868,704 A | 2/1999 | Campbell et al. | |
| 5,868,778 A | 2/1999 | Gershony et al. | |
| 5,876,375 A | 3/1999 | Penny | |
| 5,876,912 A | 3/1999 | Crawley et al. | |
| 5,879,361 A | 3/1999 | Nash | |
| 5,895,405 A | 4/1999 | Inderbitzen | |
| 5,899,935 A | 5/1999 | Ding | |
| 5,906,606 A | 5/1999 | Chee et al. | |
| 5,913,854 A | 6/1999 | Maguire et al. | |
| 5,916,153 A * | 6/1999 | Rhea, Jr. | 600/310 |
| 5,919,570 A | 7/1999 | Hostettler et al. | |
| 5,921,957 A | 7/1999 | Killion et al. | |
| 5,925,016 A | 7/1999 | Chornenky et al. | |
| 5,927,345 A | 7/1999 | Samson | |
| 5,935,122 A | 8/1999 | Fourkas et al. | |
| 5,938,672 A | 8/1999 | Nash | |
| 5,964,797 A | 10/1999 | Ho | |
| 5,980,549 A | 11/1999 | Chin | |
| 5,997,558 A | 12/1999 | Nash | |
| 5,997,562 A | 12/1999 | Zadno-Azizi et al. | |
| 6,017,323 A | 1/2000 | Chee | |
| 6,027,475 A | 2/2000 | Sirhan et al. | |
| 6,027,508 A | 2/2000 | Ren et al. | |
| 6,027,509 A | 2/2000 | Schatz et al. | |
| 6,033,381 A | 3/2000 | Kontos | |
| 6,036,697 A | 3/2000 | DiCaprio | |
| 6,050,958 A * | 4/2000 | Dickinson et al. | 600/585 |
| 6,059,751 A | 5/2000 | Ostapchenko et al. | |
| 6,066,114 A | 5/2000 | Goodin et al. | |
| 6,068,623 A | 5/2000 | Zadno-Azizi et al. | |
| 6,074,407 A | 6/2000 | Levine et al. | |
| 6,077,244 A | 6/2000 | Botich et al. | |
| 6,080,170 A | 6/2000 | Nash et al. | |
| 6,090,126 A | 7/2000 | Burns | |
| 6,096,055 A | 8/2000 | Samson | |
| 6,120,477 A | 9/2000 | Campbell et al. | |
| 6,120,904 A | 9/2000 | Hostettler et al. | |
| 6,122,552 A | 9/2000 | Tockman et al. | |
| 6,132,824 A | 10/2000 | Hamlin | |
| 6,146,370 A | 11/2000 | Barbut | |
| 6,146,372 A | 11/2000 | Leschinsky et al. | |
| 6,156,054 A | 12/2000 | Zadno-Azizi et al. | |
| 6,159,187 A * | 12/2000 | Park et al. | 604/264 |
| 6,159,195 A | 12/2000 | Ha et al. | |
| 6,159,219 A | 12/2000 | Ren | |
| 6,165,152 A | 12/2000 | Becker | |
| 6,165,163 A | 12/2000 | Chien et al. | |
| 6,176,851 B1 | 1/2001 | Tsugita et al. | |
| 6,179,788 B1 | 1/2001 | Sullivan | |
| 6,186,181 B1 | 2/2001 | Schippl | |
| 6,186,978 B1 | 2/2001 | Samson et al. | |
| 6,190,332 B1 | 2/2001 | Muni et al. | |
| 6,190,354 B1 | 2/2001 | Sell et al. | |
| 6,193,686 B1 | 2/2001 | Estrada et al. | |
| 6,206,852 B1 | 3/2001 | Lee | |
| 6,213,995 B1 * | 4/2001 | Steen et al. | 604/527 |
| 6,270,477 B1 | 8/2001 | Bagaoisan et al. | |
| 6,273,911 B1 | 8/2001 | Cox et al. | |
| 6,302,880 B1 | 10/2001 | Schaer | |
| 6,315,757 B1 | 11/2001 | Chee et al. | |
| 6,322,534 B1 | 11/2001 | Shkolnik | |
| 6,491,720 B1 * | 12/2002 | Vallana et al. | 623/1.42 |
| 6,508,806 B1 * | 1/2003 | Hoste | 604/524 |
| 6,638,245 B2 * | 10/2003 | Miller et al. | 604/96.01 |
| 6,659,134 B2 * | 12/2003 | Navis | 138/116 |
| 6,702,782 B2 * | 3/2004 | Miller et al. | 604/96.01 |

FOREIGN PATENT DOCUMENTS

| WO | WO 96/30074 A1 | 10/1996 |
| WO | WO 99/39659 | 8/1999 |
| WO | WO 02/02162 A2 | 1/2002 |

OTHER PUBLICATIONS

Dodson, "Device Reverses Blood Flow, Prevents Embolism During Carotid Procedures;" ArteriA Medical Science Inc. at <<:http:www.medicaldata.com/mit/detail.asp? art=04120101 &MITUID=20359>>, visited on Apr. 12, 2001.

NeuroVASx', Acute Stroke Initiatives: Neuro Vasx Sub-Microinfusion Catheter, at <<http:www.neurovasx.com/products.html>>, visited on Apr. 17, 2001, pp. 1-3.

* cited by examiner

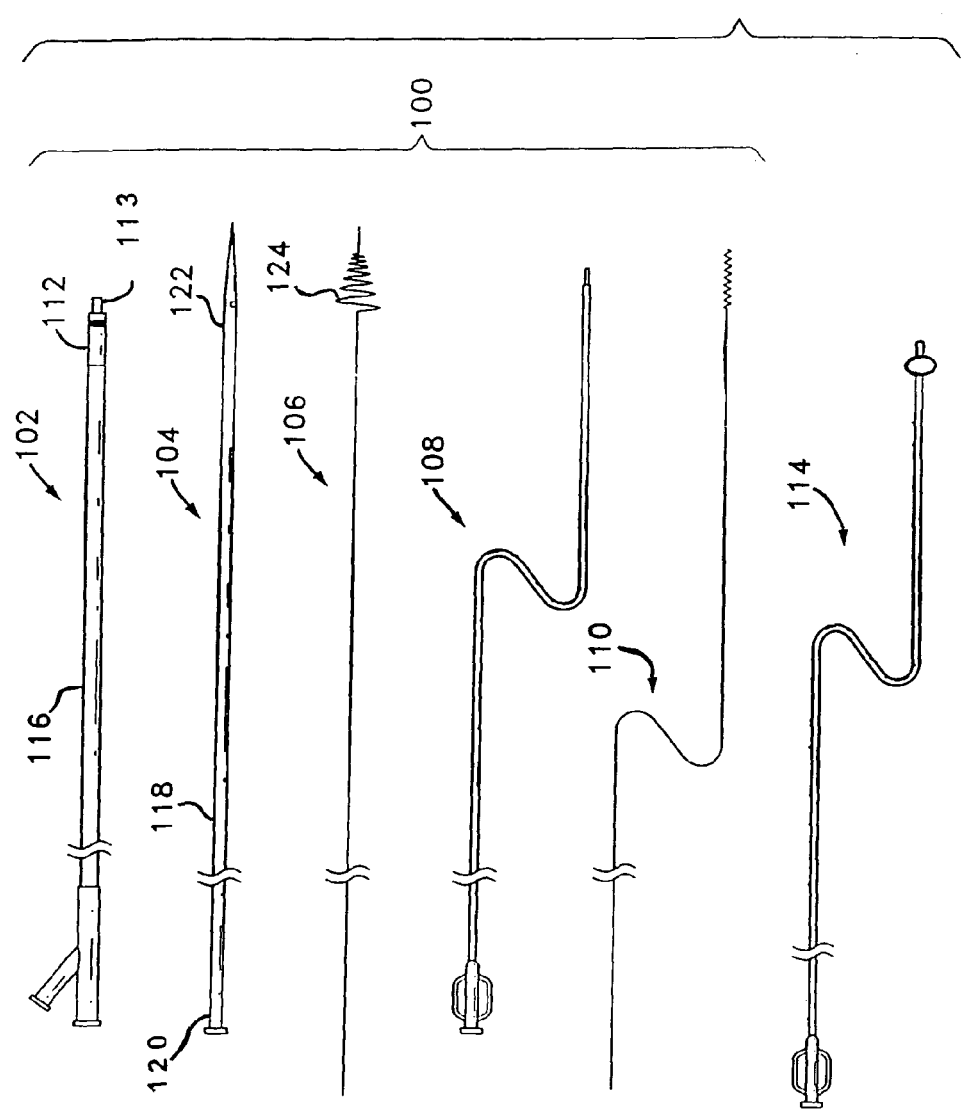

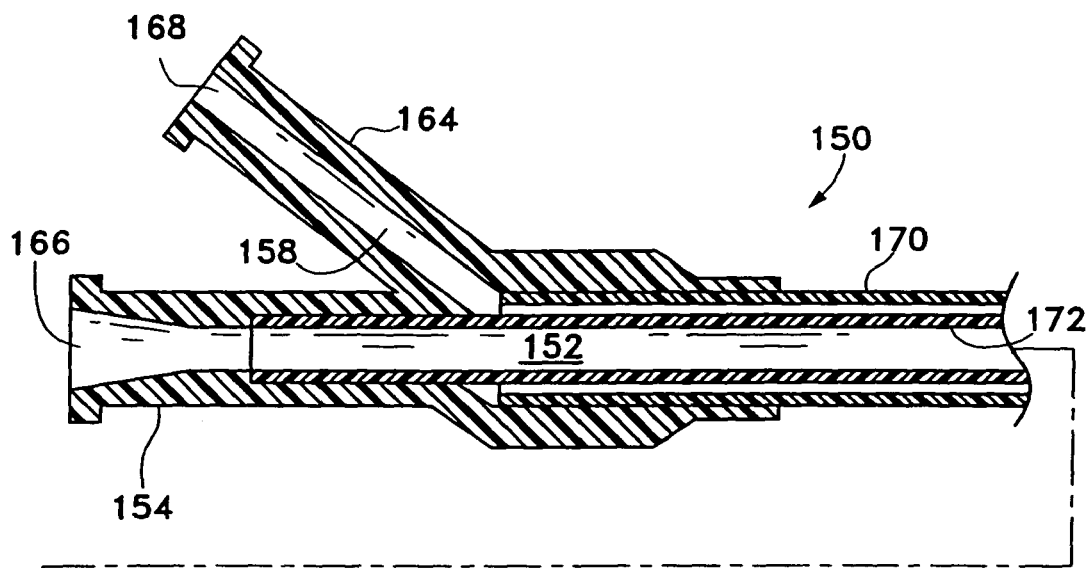
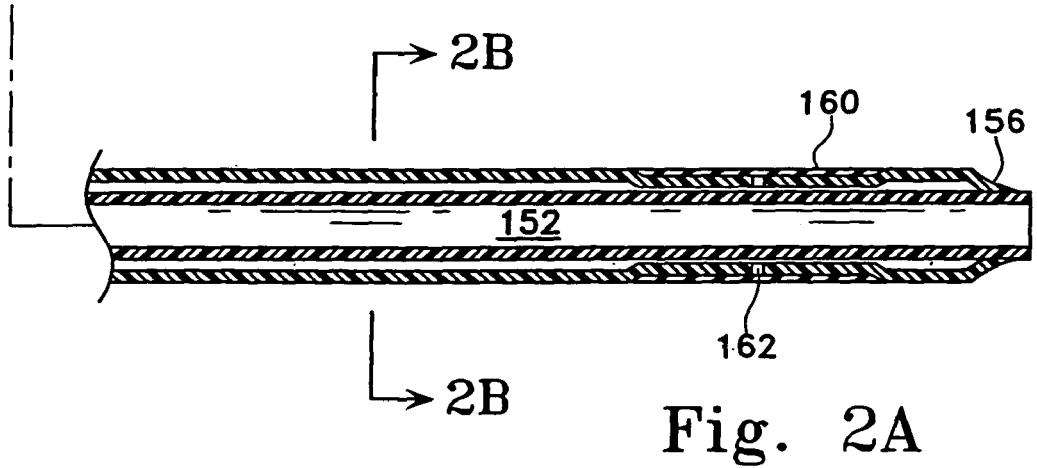
Fig. 2A
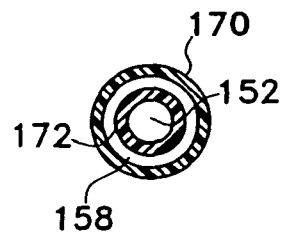
Fig. 2B

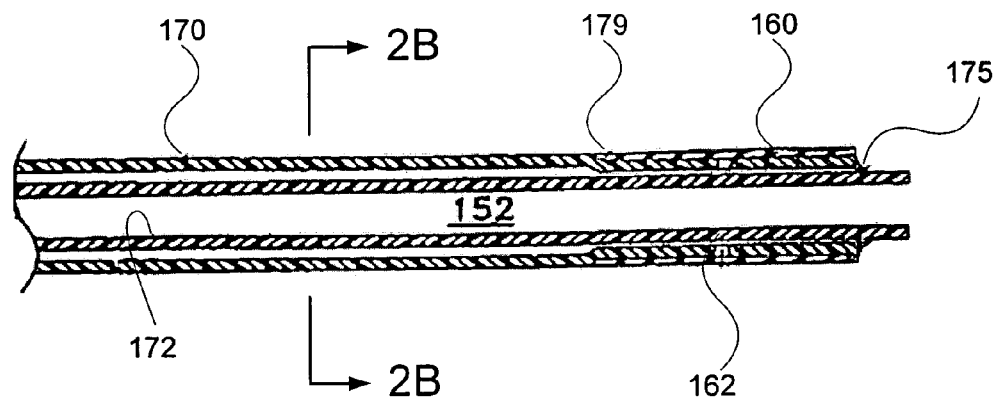
Fig. 4C
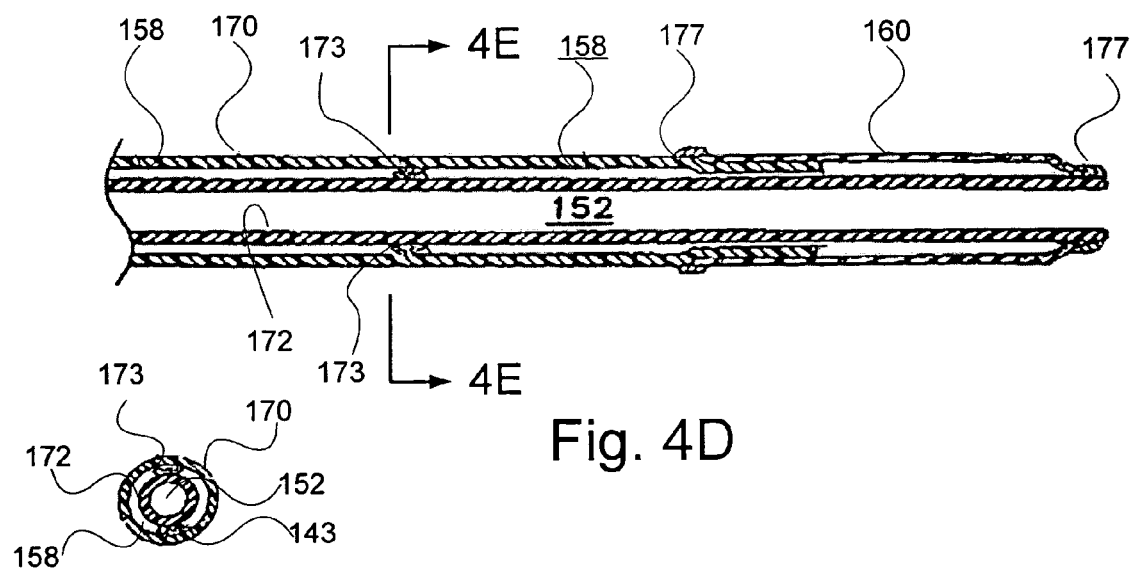
Fig. 4D
Fig. 4E

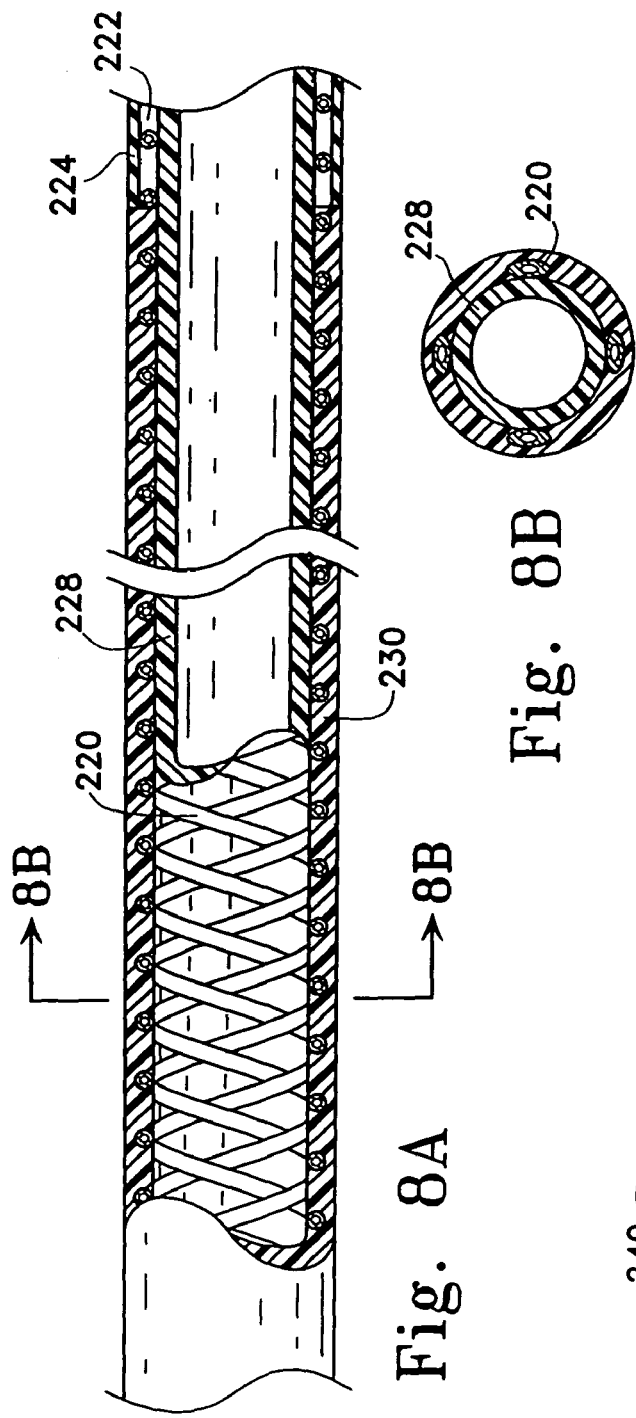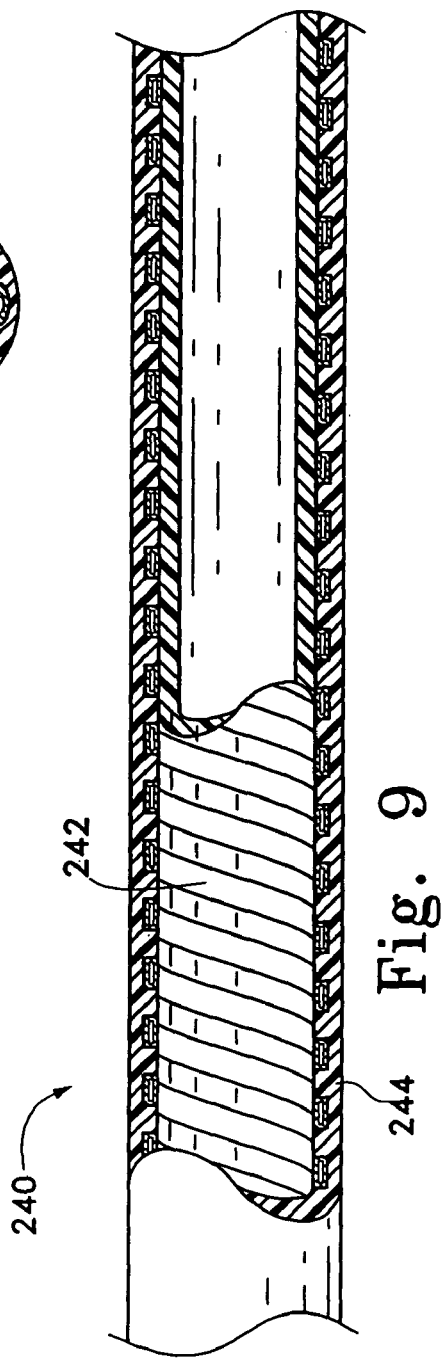

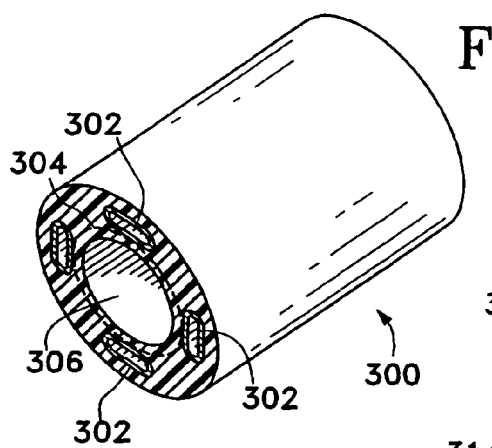
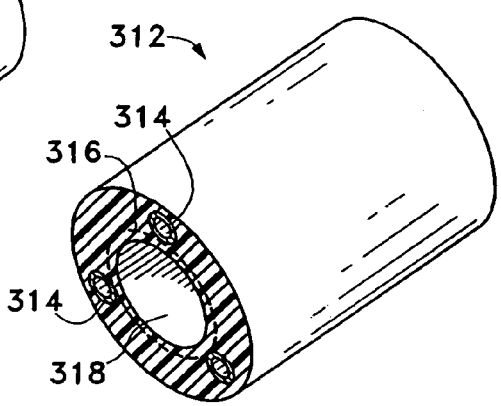
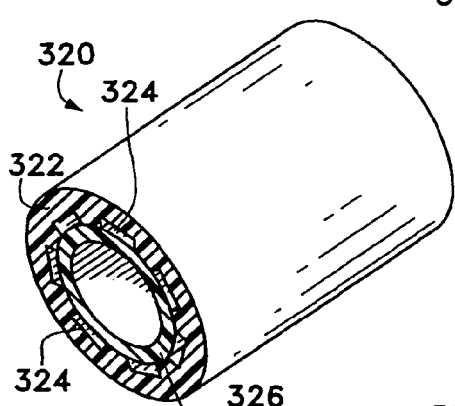
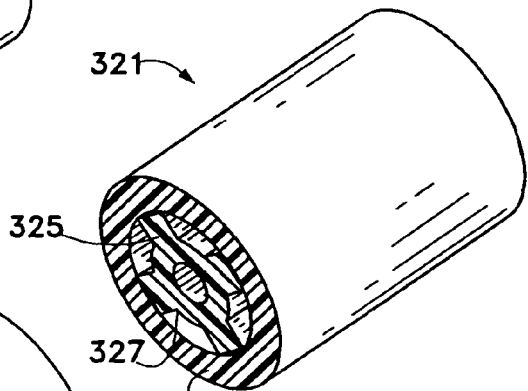
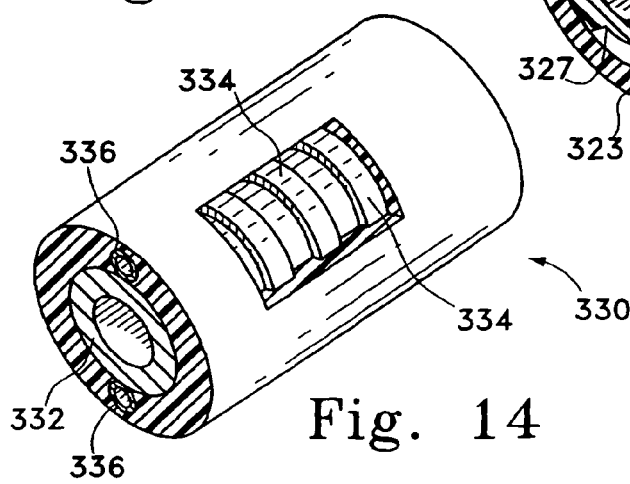

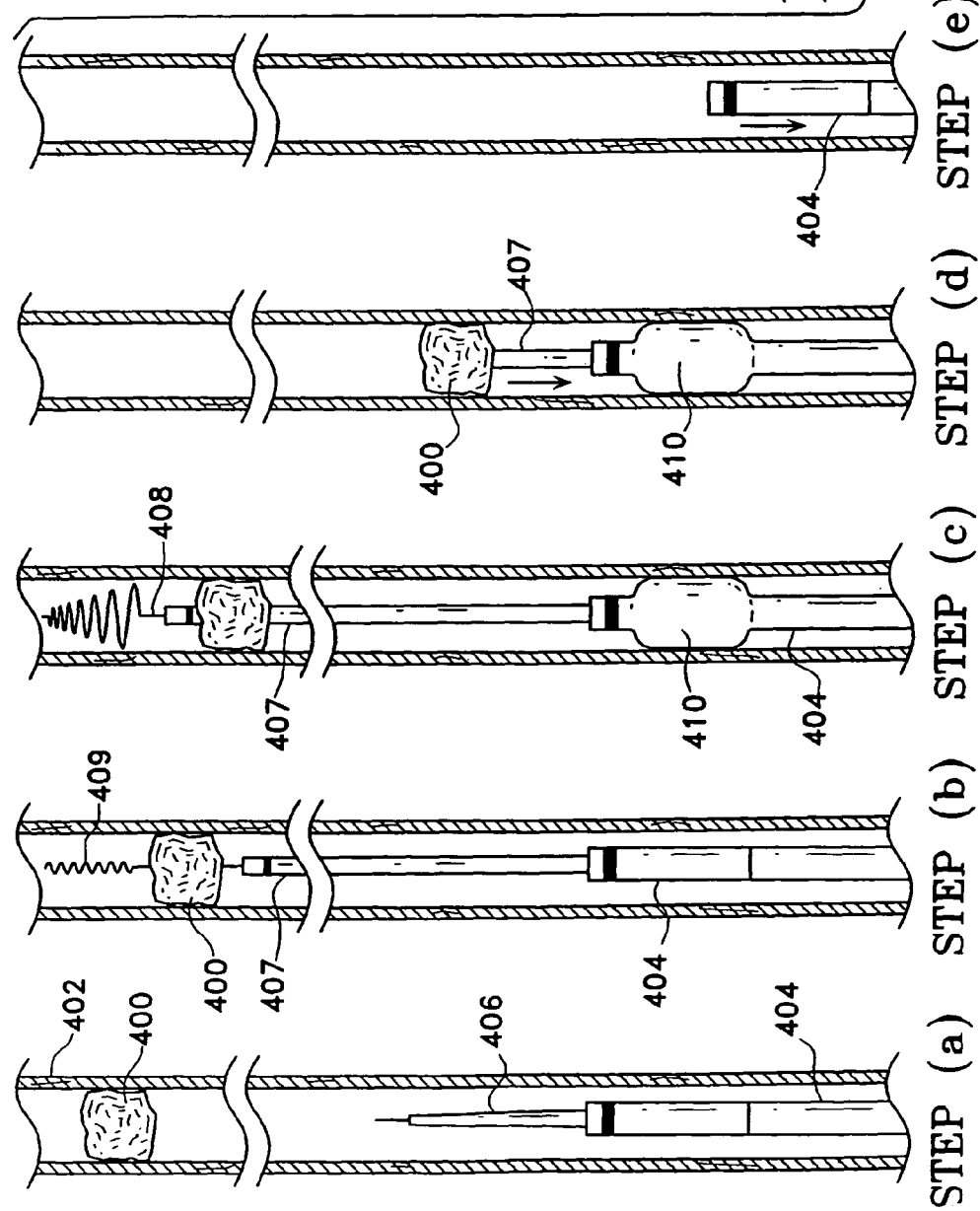

BALLOON CATHETER

CROSS-REFERENCES TO RELATED APPLICATIONS

This application is a continuation of U.S. application Ser. No. 10/085,589, filed on Feb. 28, 2002, which was a continuation-in-part U.S. application Ser. No. 09/892,349 filed on Jun. 26, 2001, the full disclosures of which are incorporated herein by reference.

BACKGROUND OF THE INVENTION

This invention is a medical device. In particular it is a balloon catheter having at least two lumens. One of the lumens is a large working lumen. The inventive catheter is especially useful as a guide catheter or a micro catheter and may be used in a variety of therapeutic and diagnostic procedures variously in the neuro-, peripheral, and coronary vasculature. In particular, it has value in treating neurovascular embolic strokes in combination with other devices which are delivered to the stroke site through the working lumen. The remainder of the lumens typically are used to inflate and to deflate the balloon. It is highly preferable that the balloon or inflatable member be situated in a recess in the outer wall of the inventive catheter. The distal end of the catheter past the balloon may be tapered. The inventive device has a very low profile as compared to other catheters of the balloon catheter genre. It may include other features such as variable stiffness along the axis of the device and anti-kinking components. The balloon may be compliant in nature.

When intended for use in treating embolic stroke, the inventive catheter may be a component of a kit including a clot retriever. Further, amongst other procedures, the invention includes methods of temporarily blocking a vascular lumen, of removing coronary, neurovascular, or peripheral emboli. Other procedures, where diagnosis or treatment is needed in a vascular space and a large working lumen is desired, are suitable procedures for the inventive balloon catheter.

This invention relates generally to medical balloon catheters, their structures, and methods of using them. In particular, the present invention relates to the construction of both large and small diameter, typically braid-reinforced balloon catheters having controlled flexibility, a soft distal tip and a typically elastomeric balloon near the distal tip for the partial or total occlusion of a vessel. This catheter has a comparatively large working lumen and carries at least one inflation lumen independent of the working lumen. The inventive catheter may be used for a wide variety of medical applications, such as interventional cardiological, peripheral, or neuroradiology procedures, but is particularly useful in support of intercranial selective catheterization.

Medical catheters are used for a variety of purposes, including interventional therapy, drug delivery, diagnosis, perfusion, and the like. Catheters for each of these purposes may be introduced to target sites within a patient's body by guiding the catheter through the vascular system, and a wide variety of specific catheter designs have been proposed for different uses.

Examples of the present invention are large lumen balloon catheters used in supporting procedures that, in turn, use small diameter tubular access catheters. Such procedures include diagnostic and interventional neurological techniques, such as the imaging and treatment of aneurysms, tumors, arteriovenous malformations, fistulas, and the like. Practical treatment of embolic stroke is novel.

The neurological vasculature places a number of requirements on the small catheters to be used there. The catheters should be quite fine. The blood vessels in the brain are frequently as small as several millimeters, or less, requiring that the intervening catheters have an outside diameter as small as one French (0.33 mm). In addition to small size, the brain vasculature is highly tortuous, requiring neurological catheters to be very flexible, particularly at the distal ends, to pass through the regions of tortuosity. The blood vessels of the brain are quite fragile, so it is desirable that the catheter have a soft, non-traumatic exterior to prevent injury.

Similarly, catheters used in supporting these procedures have similar requirements. Balloon catheters used in directing the smaller neurovascular catheters desirably have thin walls and are easily maneuverable. The central, or "working" lumen desirably is quite large to assist in effecting the procedures.

Although the peripheral and coronary vasculature is typically not as small nor as tortuous as is the neurovasculature, the advances in neurovascular catheter technology is quite applicable in advancing these procedures as well.

Typical of balloon guide catheters are those shown in U.S. Pat. No. 5,628,754, to Kranys; U.S. Pat. No. 5,833,659, to Kranys; U.S. Pat. No. 5,836,912, to Kusleika; U.S. Pat. No. 5,681,336, to Clement et al; and U.S. Pat. Nos. 5,759,173 and 5,728,063, both to Preissman et al. None of these patents show the structure disclosed herein.

BRIEF SUMMARY OF THE INVENTION

This invention involves a balloon catheter. The balloon is situated distally on the catheter body. The inventive catheter typically has a large working lumen extending from one end of the catheter to the other. The outer surface of the balloon may have a substantially constant outside diameter. The balloon is situated in a recessed region at the distal end often just proximal of a soft, tapered tip.

An example of the inventive balloon catheter is made up of an outer or first elongate tubular member having an outer surface, a proximal end, and a distal end. In this variation the first elongate member has the noted substantially constant diameter and the radially recessed region near the distal end containing the balloon. As an example, the balloon may be a longitudinally stretched inflatable member situated within the radially recessed region. The balloon, may be compliant, is connected to at least one fluid supply lumen that is independent of the working lumen. When compliant, the balloon may be stretched longitudinally at least 10%, perhaps 15% or more, upon attachment to the first elongate tubular member. Exemplary materials for the balloon include natural and synthetic rubbers and silicone materials. Chlorinated Neoprene materials such as Chronoprene or C-Plex are suitable balloon materials.

The balloon itself may be coated with various materials. For instance, the balloon may be coated with a hydrophilic material. One exemplified hydrophilic coating comprises sodium hyaluronic salt. Similarly, coatings based upon polyvinylprolidone (PVP) or polyurethane may be used. Hydrophilic coating materials such as SLIP-COAT, GLIDE-COAT, GRAFT-COAT by STS Biopolymers Inc., SLIPSKIN by MCTec, HYDRO-SLIP C by CT Biomaterials, a division of Cardio Tech International, ARMORGLIDE from ARROW, and the like are suitable.

In this variation, a second (or inner) elongate tubular member that is substantially concentric with the first elongate tubular member forms an annular lumen between the two for supplying fluid to the balloon. The interior surface of the inner elongate member forms the working lumen.

The first elongate member joins the second elongate tubular member distal of the balloon.

The second elongate tubular member generally contains a stiffener member situated in its wall to provide kink resistance and torqueability to the balloon catheter. The stiffener member may be a coil or a braid. The inner member may have varying stiffness between its distal and its proximal end, being formed of segments of polymers having different stiffnesses.

In other variations of the inventive catheter, the first elongate tubular member has a wall that contains one or more fluid supply lumens for inflating the balloon. Those fluid supply lumens may be within tubing, perhaps spirally embedded in the wall or perhaps a woven braid embedded in the wall. The tubing may be square tubing or round tubing or other convenient shape. The tubing may be polymeric or metallic. The metallic tubing may be a superelastic alloy.

Ancillary features, e.g., radio-opaque marker bands distal of said inflatable member and fluid fittings, are included.

The second elongate tubular member may include a lubricious, polymeric tubular inner-most tubing member.

Another subgeneric variation of the inventive catheter has the fluid supply lumens in the wall of the first tubing member. The lumens may be integral with the wall, e.g., passageways integral in or grooved into the first elongate tubular member and closed by an inner lubricious tubing.

Although the inventive balloon catheter desirably is used as a guide catheter, it may be designed with a flexibility, length, and diameter appropriate for use as a neurovascular, coronary, or peripheral microcatheter.

The outer member may be formed of polymeric tubing, but may also include a braid or helically wound coil of wire or ribbon.

An independent portion of the invention includes a braided tubular structure made up of a plurality of component tubular members each having longitudinal lumens, woven radially in and out to form the substantially tubular braided structure, potentially ending at one end in a plenum. The braided tubular structure may be made up of, e.g., polymeric tubing, metallic tubing (perhaps a superelastic alloy of nickel and titanium, such as nitinol). The braided tubular structure may also include at least one polymeric tubular member on its exterior. The size and shape may be useful in devices suitable for introduction into a human blood vessel.

Although the inventive balloon catheters may be independently chosen for use with any number of procedures, they may also be incorporated into one or more kits tailored for a specific procedure. For instance, a kit might contain, e.g., a dilator having a lumen extending from a proximal end of the dilator to a distal end of the dilator and having a diameter closely fitting within the balloon catheter lumen; a microcatheter having a microcatheter lumen; a guidewire slideable within either the dilator lumen or the microcatheter lumen; and a clot retrieval device adapted to fit within the lumen of the balloon catheter with a retrieved clot. The microcatheter may be a balloon catheter.

Another desirable kit includes a microballoon catheter having a flexibility, length, and diameter appropriate for a neurovascular microcatheter, a guidewire slideable within the microcatheter lumen, and a clot retrieval device adapted to fit within the lumen of the balloon catheter and extend to a radially expanded state.

The catheter may be used in a variety of procedures such as removing an embolus from a vascular lumen, e.g., in sites as varied as the middle cerebral artery, the periphery, or the coronary vessels, by the steps of: introducing the balloon catheter to a position proximal said embolus, extending a microcatheter from the distal end of said balloon catheter to penetrate the embolus, extending a clot removal device through the embolus past the microcatheter, inflating the balloon of the balloon catheter to temporarily occlude the vascular lumen, withdrawing the microcatheter, the clot removal device, and the embolus into or adjacent the balloon catheter, deflating the balloon, and withdrawing the retriever and embolus into the balloon catheter. In any of these procedures, the microcatheter may be a balloon microcatheter.

Other clot removal devices may be used in combination with the inventive catheter.

The inventive catheter may be used for treating a site in a vascular lumen or performing a diagnostic step in a vascular lumen by the steps of introducing the balloon catheter to a position in the lumen, inflating the balloon of said balloon catheter to temporarily occlude the vascular lumen, treating the site or performing a diagnostic step at the site, deflating the balloon, and withdrawing the balloon catheter.

Another variation of the present invention is a balloon catheter having an inflatable member mounted to both the inner and outer tubular members. In this variation, a proximal portion of the inflatable member is mounted to a radially recessed region of the outer tubular member. A distal portion of the inflatable member or balloon is mounted to the inner tubular member at a location distal to the distal end of the outer tubular member. The balloon may mounted to the tubular members such that, when deflated, the balloon is in a stretched state. Also, the outer and inner tubular members may be fixed together using glue to prevent "telescoping" movements between the members.

Another variation of the present invention includes a balloon catheter having an inner tubular member comprising a braided reinforcement layer extending from the proximal end to a point proximal the distal end of the inner tubular member. The braided reinforcement member, in this variation, terminates at a point 3 cm or less from said distal end of the inner tubular member. This inner tubular member is useful in the variations described above that do not exclude such a configuration.

The balloon or inflatable member in any of these variations may have a spherical shape when inflated or maybe a non-spherical when inflated.

BRIEF DESCRIPTION OF THE DRAWINGS

FIG. 1 shows a kit of devices including the inventive balloon catheter (used as a guide catheter) suitable for treating embolic stroke.

FIG. 2A shows, in partial longitudinal cross section, a variation of the inventive catheter. FIG. 2B shows in cross section, the variation found in FIG. 2A.

FIG. 4C shows, in partial longitudinal cross-section, another variation of the distal section of a catheter in accordance with the present invention.

FIG. 4D shows, in another partial longitudinal cross-section, yet another variation of the distal section of a catheter in accordance with the present invention. FIG. 4E shows in cross section, the variation found in FIG. 4D.

FIG. 8A shows a partial longitudinal cross section of a desirable variation using woven tubing as the inflation lumen for the balloon. FIG. 8B shows a cross section of the catheter shaft shown in FIG. 8A.

FIG. 9 shows a further variation of a catheter shaft having one or more rectangular tubes as delivery lumen for the inflatable balloon.

FIGS. 10, 11, 12, 13, and 14 show integrated variations of catheter shafts suitable for use in the inventive balloon catheter assembly.

FIG. 15 shows one procedure for using the inventive catheter and the allied kit for treatment of an embolism in an artery.

DETAILED DESCRIPTION OF THE INVENTION

Figure 3A:
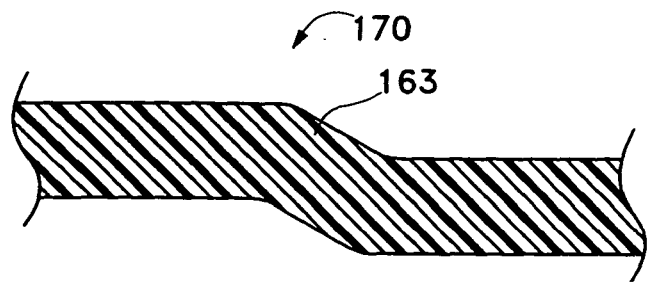
FIGS. 3A-3E show, in partial longitudinal cross-section, details of the wall construction of the outer tubular member.

The invention described here is a multi-lumen balloon catheter having a large working lumen and a distally located balloon situated in a recess in the outer surface. The device has a variety of uses depending only upon the need for a catheter having a large working lumen and the ability to block a vascular lumen for diagnosing or treating a physical malady.

FIG. 1 shows a kit (100) comprising components that likely would be used in combination to treat an embolic stroke. The kit (100) shown in FIG. 1 includes the inventive balloon catheter (102) (here used as a guide catheter), a dilator (104), a clot retrieval device (106), and an optional microcatheter (108). Optionally, the kit may include a guidewire (110) for use in guiding the microcatheter (108) to a selected site.

In overall concept, our balloon catheter (102), by example, is a thin walled or low profile catheter having a distal inflatable member or balloon (112). A small section (114) distal of the balloon may be soft and tapered from the outside diameter of balloon (112). In one variation, the catheter shaft (116) is of a single diameter. The balloon (112) may be situated in a recess in the outer wall of the catheter shaft (116) so that the balloon (112), prior to inflation and after deflation, has the same or smaller approximate diameter as does the catheter shaft (116).

Additionally, balloon catheter (102) has at least two lumens. One lumen is a large working lumen for introduction of the other portions of the kit and whatever other devices and materials are to be introduced to the selected vascular site and one or more lumens for directing inflation fluid to balloon (112). The inventive balloon catheter (102) often includes two lumens, the fluid supply lumen being an annular space between an inner and an outer tubular member. Other variations of the fluid supply lumen arrangement are discussed below.

Dilator (104) is a component typically having an extended shaft which fits snugly, but movably, inside the working lumen of inventive catheter (102) but is able to slide easily through that working lumen. Dilator (108) has a lumen from its proximal end (120) to its distal end (122). Distal end (122) is conical and the lumen in the middle of dilator (104) extends from the distal end (122) and is open axially. Inventive catheter (102) and dilator (104) are desirably cooperatively sized so that the conical distal region (122) of dilator (104) is extendable beyond the distal end of catheter (102).

Dilator (104) generally is for the purpose of spanning the gap between the guidewire used to direct balloon catheter (102) and the interior surface of balloon catheter (102). It provides stability to that guidewire.

One highly desirable embolus retrieval device (106) suitable for use in this kit is described in greater detail in U.S. patent application Ser. No. 09/605,143, filed Jun. 27, 2000, the entirety of which is incorporated by reference. Again, in overall concept, the clot removal device (106) is carefully tailored to engage a thrombus using the microcatheter (108) and, once the microcatheter (108) tip is downstream of the embolus, the clot retrieval device (106) is extended from encasing microcatheter (108) to allow formation of the spiral enveloping region (124) shown in FIG. 1. Desirably, balloon (112) is inflated temporarily to prevent potential for bloodflow or for a "water hammer" effect in the artery of concern. The retriever (106), with its then-included clot enveloped in a coil-like region (124), is then pulled back into the balloon catheter (102).

Other known clot retrieval devices are, of course, acceptable for inclusion in these kits.

In any event, the balloon (112) is then deflated and removed with the then-included offending emboli.

The kit may include, either as an alternative to microcatheter (108) or as an addition to the microcatheter (108), a balloon microcatheter (114) often of the design described herein or other suitable design. The balloon microcatheter (114) maybe inflated and used in place of the microcatheter (108) to stop blood flow in that region while retrieving the thrombus.

Again, as noted elsewhere, this inventive catheter is quite valuable as a guide catheter but may be constructed in any size that meets the need of the user.

Other kits of the devices shown in FIG. 1, intended for other purposes are also contemplated, e.g., a microballoon catheter (112) made according to the invention optionally in combination with either or both of a guidewire (110) and with a thrombus retrieval device (106) is suitable for emergency stroke treatment.

Finally, the kits described here are intended to include clot retrieval devices other than the device shown in FIG. 1, although that device is preferred.

An example of the inventive balloon catheter (150) is shown in partial longitudinal cross section in FIG. 2A.

As noted above, the inventive device has at least two lumens. In this variation the working lumen (152) extends from the proximal end of the device (154) to the distal end of the device (156) and is open at that distal end (156). In this variation, the fluid conveyance lumen (158) is annular and connects fluidly with inflatable member or balloon (160) via a number of orifices (162).

FIG. 2B provides a cross section of the variation shown in FIG. 2A and provides a depiction of working lumen (152) and fluid flow lumen (158).

A Y-shaped fluid control and access device, e.g. a Luer-Lok (164), is shown in FIG. 2A. Fluid access device (164) has an opening (166), which accesses only working lumen (152) and further includes an opening (168), which accesses only the annular lumen (158). We provide a large working lumen and one or more fluid delivery lumens by, in turn, providing a first or outer elongate tubular member (170) concentrically surrounding a second or inner elongate tubular member (172). By placing the inner member (172) within the outer member (170), an annular fluid supply lumen (158) is created. Spot welds and adhesives may be used to tack the inner and outer tubular members together, a structure that is useful when the balloon or inflatable member is attached to the inner and outer members. Working lumen (152) extends axially the length of inner member (172). In this variation, outer elongate member (170) is a polymeric tubing member having a substantially constant diameter from one end to the other with certain exceptions as described hereinafter. An exception is that a region near or adjacent the distal end (156) is recessed in such a way that a balloon or inflatable member (160) may be glued or solvent welded or otherwise made to adhere to the first member (170) at the ends of the recessed region.

Additionally, the distal portion of outer member (170) is desirably tapered at its most distal end (156) and joined to inner member (172). Typically, outer member (170) is a single piece of a polymeric tubing produced from material that is used in devices of this type. Materials of construction are desirably polyurethane (e.g., Pellaflex and Pellathane), polyether-polyamide block copolymers (e.g., Pebax), polyethylene (e.g., HDPE, LDPE, and LLDPE), and others, usually having significant flexibility.

Figure 3B:
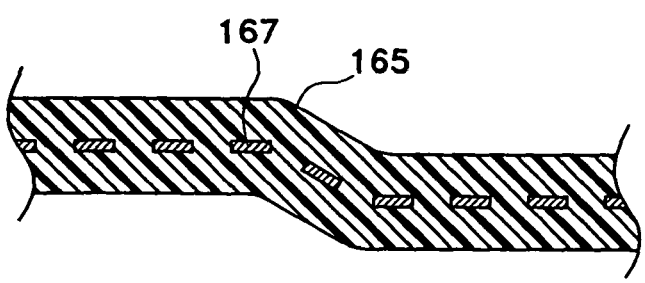
Figure 3C:
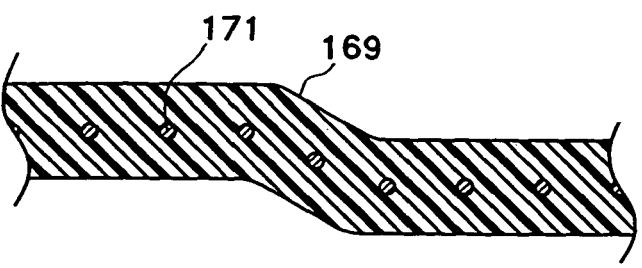
Figure 3D:
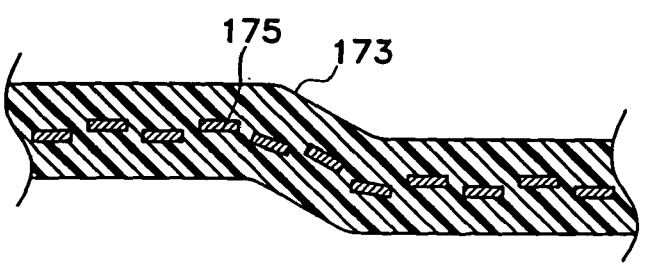
Figure 3E:
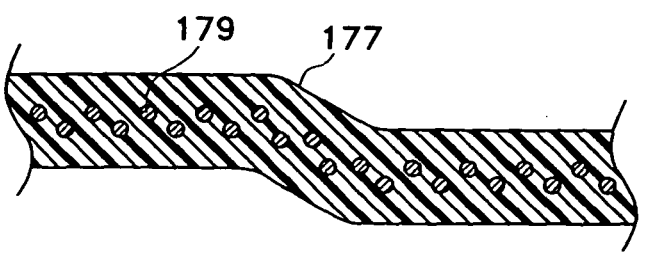

In one variation, the outer tubular member (170) has a substantially constant outer diameter. In another variation the outer tubular member (170) has a first section and at least one other distal section of smaller outer diameter. Also, the inner diameter of the outer tubular member (170) may be constant or may vary. The outer tubular member (170) may contain a material having a constant Durometer value and have a generally constant wall thickness, e.g., +/−0.002 inches. However, the invention is not so limited and the outer tubular member (170) may have a varying wall thickness and the contained material may have a varying Durometer value. As shown in partial longitudinal cross-section in FIG. 3A, although one example of the outer elongate member (170) may be of a neat polymer tubing (163) for a variety of reasons expressed elsewhere, other wall compositions are acceptable and may even be desirable for some usages. FIG. 3B shows, in partial longitudinal cross-section, an outer elongate member wall (165) containing a helically placed ribbon coil (167). FIG. 3C shows, in partial longitudinal cross-section, an outer elongate member wall (169) containing a helically placed wire coil (171). FIG. 3D shows, in partial longitudinal cross-section, an outer elongate member wall (173) containing a woven ribbon braid (175). Finally, FIG. 3E shows, in partial longitudinal cross-section, an outer elongate member wall (177) containing a woven wire braid (179). Any of the ribbon and wire discussed here may be variously metallic (e.g., stainless steels or superelastic alloys such as nitinol) or polymeric. The polymers may be single phase, e.g., such as monofilament line, or multiple strands bundled or woven together. These components may be made of a mixture of materials, e.g., super-elastic alloy and stainless steel components or of liquid crystal polymers (LCP's). For cost reasons, strength, and ready availability stainless steels (SS304, SS306, SS308, SS316, SS318, etc.) and tungsten alloys may be used. In certain applications, particularly in smaller diameter devices, more malleable metals and alloys, e.g., gold, platinum, palladium, rhodium, etc. may be used. A platinum alloy with a few percent of tungsten or iridium is sometimes used because of its high radio-opacity.

When using a super-elastic alloy in any of the component tubing members, an additional step may be desirable to preserve the shape of the stiffening braid or coil. For instance, after a braid has been woven using, e.g., 4, 8, 12, or 16 members, some heat treatment may be desirable. Braids which are not treated this way may unravel during subsequent handling or may undertake changes in diameter or spacing during that handling. In any event, the braids are placed on a heat-resistant mandrel, perhaps by weaving them onto that mandrel, and placed in an oven at a temperature of, e.g., 650.degree. to 750.degree. F. for a few minutes. This treatment may anneal the material in the constituent ribbon or wire but in any event provides it with a predictable shape for subsequent assembly steps. After heat-treatment, the braid does retain its shape and most importantly the alloy should retain its super-elastic properties.

Figure 4A:
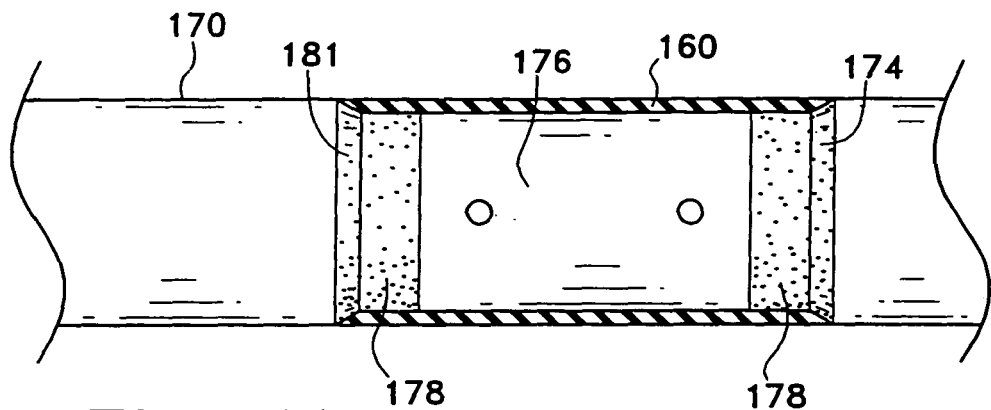
FIGS. 4A and 4B show, in partial longitudinal cross section, details of the inflatable member construction.
Figure 4B:
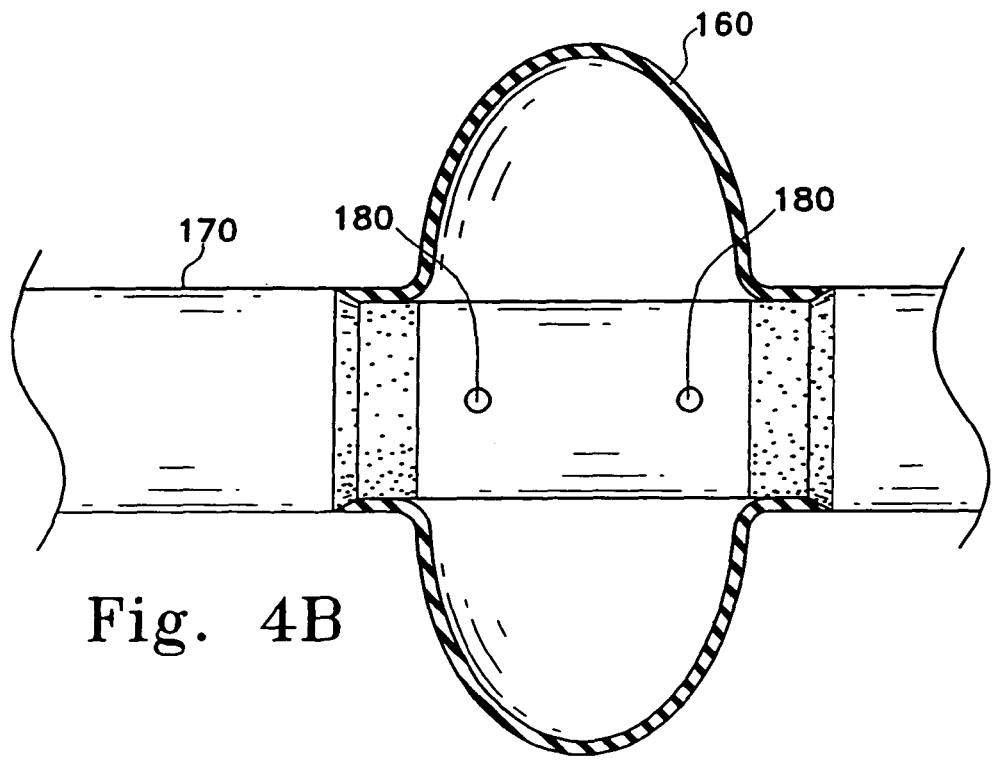

FIGS. 4A and 4B show the mounting of the balloon in a radial depression in greater detail. In FIG. 4A, two shoulders (181) and (174) may be seen rimming the depressed or recessed region (176). Also shown in the partial cutaway views found in FIGS. 4A and 4B are two regions (178) in which the recessed area (176) is etched or roughened so to permit better adhesion of the balloon material. Balloon (160), again, is only adherent to the recessed region (176) at roughened regions (178). FIG. 4B shows balloon (160) in an inflated state after a fluid passes through orifices (180) into inflatable member (160). To reiterate, deflated balloon (160), as seen in FIG. 4A, has the same approximate diameter as does substantially all of the rest of outer member (170).

However, as indicated above, another variation of the present invention includes a balloon situated within the recessed region such that when the balloon is deflated, the outer diameter of the deflated balloon is less than the outer diameter of the rest of the outer tubular member. Also, it is to be understood that the outer tubular member may have a varying outer diameter (e.g., be necked-down) in some variations. In one exemplary variation, the outer tubular member can have a first proximal section of a first outer diameter and a second distal section of a different (e.g., smaller) outer diameter. The distal section may further include a recessed region as described elsewhere in this application.

The orifices (180) may be of any convenient shape, e.g., oval, square, etc. Indeed, they may be spiral cuts or the like.

The shape of the inflated balloon (160) may vary widely. In one variation, the inflated balloon (160) has a spherical shape. The inflated balloon (160) however, may have a non-spherical shape. For instance, the inflated balloon may have an oval, elongate, cylindrical, non-spherical or other shape. The balloon (160) may be expanded to a radius from 0.02 to 0.60 in., or perhaps from 0.04 to 0.40 in. The length of the balloon (160) typically corresponds to the length of the recessed region (176) and is perhaps from 3 to 15 mm or perhaps from 5 to 10 mm. However, other dimensions may be chosen depending upon the application and the size of the vessel to be operated on. The balloon may have a constant or non-constant wall thickness.

Another variation of the present invention is shown in FIG. 4C. In FIG. 4C, balloon 160 is disposed across a radially recessed region (176) of outer tubular member (170). Unlike the recess shown in FIGS. 4A-4B, the recess (176) shown in FIG. 4C lacks a distal or return shoulder (174). The recess shown in FIG. 4C thus features only one proximal shoulder (179). In this variation, the length of the recess may be less than 7 mm or perhaps less than 3 mm.

The distal end of outer tubular member (170) may be secured, formed, or sealed to inner tubular member (172) using heat, adhesives, glues, marker bands or other adhering methods to form a fluid tight seal (175). Fluid may be introduced through aperture (162) to inflate balloon (160) as noted above. Additionally, the end of the outer tubular member (170) may be tapered onto inner tubular member (172) to lower the device's distal profile.

FIG. 4D shows another variation of the present invention. As shown in FIG. 4D, balloon (160) joins the distal end of outer tubular member (170) to inner tubular member (172). In this variation, a proximal portion of balloon (160) is situated in a recessed region of the outer tubular member and a distal portion of the balloon is mounted to the inner tubular member. As noted in the above discussed variations, an annular inflation lumen (158) may be defined between outer tubular member (170) and inner tubular member (172) and is in fluid communication with the balloon (160). To expand the balloon (160), fluid is introduced through the annular inflation lumen (158) and into a chamber formed by balloon (160). The balloon (160) may have a somewhat tapered distal end in its deflated shape to provide a low profile design.

As shown in FIGS. 4D and 4E, discrete amounts of adhesive or glue (173) may be included to bond or fix the inner tubular member (172) to outer tubular member (170). The glue prevents "telescoping" movements between the tubular members. Also, glue spots (173) are sized and positioned in inflation lumen (158) such that they do not form significant flow restrictions in that inflation lumen (158). FIG. 4E shows a suitable configuration for the glue spots (173). However, the location of glue spots (173) may vary widely and the adhesive may be disposed generally anywhere along the length of the inflation lumen (158.) The adhesive (173) may be disposed at more than one location along the length of the inflation lumen (158).

Also, plugs of material similar to that used to make the inner and outer tubular members may be used to heat fuse the inner and outer tubular members together.

Radio-opaque marker bands (177) may be attached to the balloon catheter to aid visualization of the balloon catheter, and particularly, the ends of the balloon (160) and to determine its location. Marker bands (177) may be placed partially or completely on the balloon (160) or adjacent the balloon. FIG. 4D shows marker bands (177) placed partially on balloon (160) and partially on another component of the device.

The marker bands (177) may by raised from the surface of the outer diameter surface of the catheter as shown in FIG. 4D or assembled flush with the outer diameter of the outer tubular member (170). The marker bands (177) may be swaged flush with the outer diameter of the outer tubular member (177) to minimize the device's profile. Suitable materials for the marker bands include metals and alloys that are radio-opaque. Examples of such metals and alloys include platinum and platinum alloys.

Figure 5:
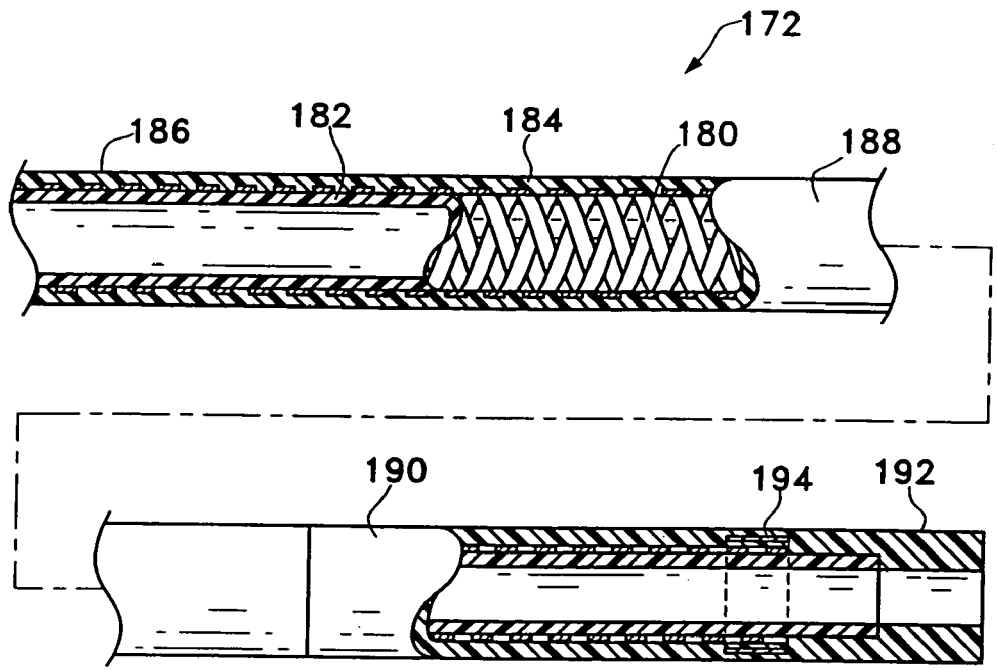
FIGS. 5, 6, and 7 show variations of the interior tubular member.
Figure 6:
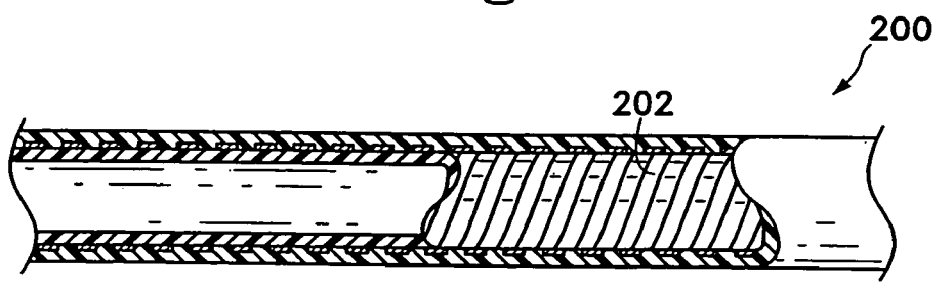
Figure 7:
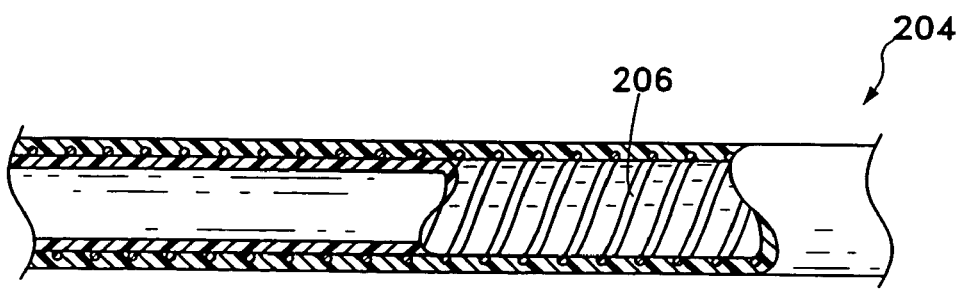

FIGS. 5, 6, and 7 show variations of the component found in the above discussed Figures as the inner elongate member (172). Inner elongate member (172), in this variation of the invention, desirably provides two important functions to the inventive catheter. Those functions are kink resistance and increasing flexibility towards the distal end of the inventive catheter. Although in other variations of the invention, such functions may be provided by the outer member, provision of these functions in the inner member allows significant economy in profile and allows for significantly greater overall flexibility and consequent ease of access to distant neurovascular locations.

FIG. 5 shows a variation comprising a braid (180), an inner liner (182) and an outer covering (184). The braid (180) is formed from ribbons of stainless steel, superelastic alloys such as nitinol, or polymeric constructs. Although the braid may alternatively be formed from a round or oval profiled wire, a ribbon has an overall lower profile attainable with an enhanced amount of kink resistance. For this variation, stainless steel ribbon braid is exemplified. The ribbon making up the braid may be less than 1.5 mil in thickness, perhaps 0.7 mils to 1.5 mils, or perhaps about 1 mil. The width may be 2.5 mils to 7.5 mils in width, often about 5 mils. By "braid" here, we mean that the braid components are woven radially in and out as they progress axially down the braid structure. This is to contrast with the use of the term "braid" with co-woven coils merely laid one on top of the other in differing "handedness."

Inner liner (182) desirably is a very thin, e.g., 0.25 mil to 1.5 mil wall thickness, of a hard or lubricious material such as a polyfluorocarbon. Such lubricious polymers include polytetrafluoroethylene (PTFE or TFE), ethylene-chlorofluoroethylene (ECTFE), fluorinated ethylene propylene (FEP), polychlorotrifluoroethylen-e (PCTFE), polyvinylfluoride (PVF) or polyvinylidenefluoride (PVDF). PTFE may be used. Other materials such as polyethylene (particularly HDPE), polypropylene, and polyamides (the Nylons) their mixtures and copolymers are also acceptable.

The outer covering (184) may be of a significantly softer material than is that making up the inner liner (182). Moreover, the material making up the outer covering (184) be thermoplastic so to allow melting into the braid (180) or other stiffening or anti-kinking member. Materials include polyethylene (LDPE and LLDPE), polyvinylchloride (PVC), ethylvinylacetate (EVA), polyethylene terephthalate (PET), and their mixtures and copolymers. Also suitable are thermoplastic elastomers, particularly polyesters. Typical of this class is HYTREL. Polyurethanes such as Pellethane are suitable. Another copolymer of polyurethane and polycarbonate sold as Carbothane also works well. Especially desirable, though, is a block copolymer of polyethers and polyamide commercially known as PEBAX.

Additionally, the stiffness of the inner elongate member (172) may be varied. One method for varying the stiffness is by choice of polymers having different stiffnesses as (practically) measured by Shore Durometer values. In the variation shown in FIG. 5, the outer covering (184) is made up of four distinct polymer sections. The most proximal portion (186) desirably has a Shore Durometer hardness of 65 to 78 D, such as about 72 D. The next more distal portion (188) may be made up of a polymer having a Shore Durometer hardness of 50 to 60 D, such as about 55 D. The next more distal portion (190) may have a Shore Durometer hardness of 35 to 45 D, such as about 40 D. The most distal section (192) may have the softest Shore Durometer hardness, between 30 and 40 D, e.g., about 35 D. Again, these are in keeping with use in the neurovasculature. However, other uses would allow other stiffnesses.

In the variation shown in FIG. 5, proximal section (186) has a length of about 85 to 115 centimeters, perhaps about 95 to 105 centimeters, and perhaps about 100 centimeters. The next more distal section (188) may have a length of about 20 to 40 millimeters, perhaps about 25 to 35 millimeters or perhaps about 30 millimeters. The next more distal section (190) may have a length of about 50 to 60 millimeters, perhaps about 45 to 55 millimeters, or perhaps about 50 millimeters. Finally, the most distal portion may be quite short at about 1 to 10 millimeters, perhaps about 3 to 6 millimeters, or perhaps about 4 millimeters. The lengths of these sections may be varied once this disclosure is appreciated by those having ordinary skill in this art. The lengths may also be varied to optimize the necessary performance characteristics of a guide catheter or microcatheter.

The braid in this variation may terminate beneath a radio-opaque marker (194) located fairly distally on inner elongate member (172). In one exemplary variation, the braid terminates within 3 cm and perhaps, 1 cm or less, from the distal end of the elongate member (172). However, the invention is not so limited and the braid may terminate more than 3 cm and perhaps, more than 10 cm, from the distal end of the elongate member (172).

Generally, the radio-opaque marker is a band or helically wound coil of a radio-opaque material such as platinum or a platinum-iridium alloy. It may be of other materials as desired or as appropriate. If the radio-opaque marker (194) is a metallic band, it is often assembled over a thin layer of PET to help with the adherence of the radio-opaque marker to the end of the braid (180).

Typically, the inner member (172) is assembled in the following fashion. A mandrel, having an appropriate size, is selected. The inner lubricious liner (182) is then slid onto that mandrel. As noted above, the inner layer (182) may be comprised of a material such as polyimide, polyamides such as the Nylons, high density polyethylene (HDPE), polypropylene, polyvinylchloride, various fluoropolymers (for instance, PTFE, FEP, vinylidene fluoride, their mixtures, alloys, copolymers, block copolymers, etc.), polysulfones or the like. The braid (180) is then slid onto inner liner (182), and then various outer sections of thermoplastic (186, 188, 190), the appropriately placed radio-opaque marker (194), and the distal-most portion (192) are then placed on the partially-assembled mandrel. Finally, a shrink-wrap material such as cross-linked polyethylene or a fluorocarbon (e.g., PTFE or FEP) is then placed on the outside of the assembled inner tubular member. The thus-assembled components are then subject to heat treatment at a temperature which is intended to have the effect both of shrinking the heat-shrinkable outer layer material and allowing the outer thermoplastic layers to pass their $T_g$ (glass point) and to flow into the kink resisting member, e.g., the braid (180).

Once that is accomplished, the heat-shrinkable tubing is then stripped from the assembly and the second or inner elongate tubular member (172) is ready for joining to the outer or first elongate tubular member (170) discussed above.

Additionally, the various outer sections may be dip-coated onto the inner sections using molten polymers.

FIG. 6 shows a variation (200) of the inner member which is similar in most aspects to the component (172) discussed with relation to FIG. 5 above. The difference here is the presence of helically wound coil (202) in the place of the braid (180) in FIG. 5. Similarly, FIG. 7 shows still another variation (204) of the component utilizing a helically wound wire (206) instead of the braid (180) found in FIG. 5. The braid, coil or wire need not always extend to the distal end of the elongate member and may terminate at various distances proximal to the distal end as stated above with respect to FIG. 5. In certain variations of the present invention, therefore, the distal section of the inner elongate tubular member is unreinforced by a braid, coil or wire.

Another variation of the inventive balloon catheter is a subgeneric category in which the functions of the inner longitudinal member and the outer longitudinal member spoken of in the variations above are merged into a single wall. That is to say that the annular fluid supply lumen (158) is not present in these variations and the fluid supply lumens may be those found in multiple fluid supply tubing components or extruded into the wall of the elongate lumen tubular member. In general, there is no second elongate tubular member in this set of variations.

FIGS. 8A, 8B, and 9 show variations of the invention in which the tubing which serves as the kink resistant member further serves as its fluid supply conduit.

FIGS. 8A and 8B show, respectively, a partial longitudinal cross-section and a full radial cross-section. Also seen is the placement of braided tubing terminating in a small plenum (222) just beneath the inflatable member diaphragm (224). The fluid used to inflate the balloon (224) passes through each of these tubing members (220) and conversely to deflate inflatable member (224) along the same path.

A plenum may be found at the either the distal or the proximal end of the catheter for distribution of fluid to the multiple braided tubing members. As was the case above, this variation of the first elongate tubular member may include a lubricious inner member (228) or not. Similarly, the materials making up the outer layer (230) may be of the materials discussed above. The benefit of this particular design is that it eliminates many layers of parts and yet is able to maintain the inner lumen at a maximum size.

Similarly, FIG. 9 shows another variation (240) of catheter walls suitable for use in the inventive balloon catheter. In this variation, at least one or more rectangular tubing members (242), having open inner lumen, is helically placed within the catheter section wall (244) to permit fluid flow to the inflatable balloon.

The shape of the hollow tubing found in FIGS. 8A, 8B, and 9 is not limited to those seen in the drawings. Any convenient shape, e.g., round, square, rectangular, oval, etc., will suffice.

FIG. 10 shows a perspective cut-away of catheter section (300), having a plurality of passageways (302) which are used as fluid passage lumen. Kink resisting member (304), e.g., a coil, braid, multiple coils, or the like, is also shown there. A working lumen (306) is also depicted. As was the case above, the catheter section (300) may be made up of a combination having interior lubricious tubing, or may be made from a single material.

FIG. 11 shows another variation of the catheter wall section (312) useful in the inventive balloon catheter. Catheter section (312) is shown in FIG. 11 to have multiple discrete tubing members (314), which have been made integral with the wall of catheter section (312). Again, the stiffening or anti-kinking member (316) is shown to be situated exterior of the working lumen (318).

FIG. 12 shows still another variation (320) of the catheter section. In this instance, the wall is assembled by the joinder of two members. The outer member (322), typically made by extrusion, has a number of longitudinal grooves (324) placed in the outer member (322) as it is made. An inner member (326) is thereafter inserted into outer member (322) to close grooves (324) and allow them to function as fluid flow lumens to the inflatable balloon discussed above.

FIG. 13 shows a variation (321) of the catheter section shown in FIG. 12. Again, this wall is assembled in by joinder of two members. The outer member (323), is a simple smooth tubing. The inner member (325), an extrusion, has an number of longitudinal grooves (327). The inner member (325) is inserted into outer member (323) to close or to envelop grooves (327) and allow them to function as fluid flow lumens to the inflatable balloon discussed above.

FIG. 14 shows another variation (330) of the catheter wall suitable for use in the inventive balloon catheter. In this variation, a metallic tube (332) (e.g., a "hypotube") which has been machined or otherwise cut away to form interlocking teeth in one or more places around the circumference of the tube is embedded into the catheter wall section thereby allowing the tube to bend with ease. FIG. 14 shows a pair of tubing members (336) which each have interior lumens suitable for providing fluid to the inflatable balloon.

FIG. 15 shows a five-step method for deploying the inventive balloon catheter in an artery for removal of an embolism (400) from that artery (402).

In Step (a), the inventive balloon catheter (404) with dilator (406) has been placed in the occluded vessel. In Step (b), dilator (406) has been withdrawn from balloon catheter (404) and replaced with microcatheter (407) and guidewire (409). The microcatheter (407) tip is seen approaching clot (400) and the guidewire (409) has penetrated the embolus (400) and may be seen protruding from the distal side of that clot. The microcatheter may be advanced through the clot.

In Step (c), the guidewire (409) has been replaced by retrieval member (408). Retrieval member (408) has been placed distal of clot (400) and balloon (410) on inventive balloon catheter (404) has been inflated to block the flow of blood towards embolus (400). The distal end of microcatheter (407) has been urged through the clot (400) and is distal of the clot (400). Inflation of balloon (410) has several effects. First of all, it prevents blood from carrying small portions of the embolus distally for ultimate lodging in other arterial vessels. Secondly, it quells the "water-hammer" effect which may tend to break up such clots. Thirdly, when used in the brain to remove clots in the middle cerebral artery because of the unique nature of the vasculature in that portion of the brain, closing the middle cerebral artery at this point causes backflow, which may tend to push the clot (400) back towards the open lumen of catheter (404). It is understood that the microcatheter may also have a balloon.

Step (d) shows the removal of clot (400) and the retraction of the microcatheter (407) and embolism retriever (408) into the end of balloon catheter (404).

Finally, Step (e) shows the removal of balloon catheter (404) after the clot and the retrieval device have been withdrawn into the open end of catheter (404) and balloon (410) deflated.

The specific example described in conjunction with FIG. 15 is for the purpose of showing the practical utility of the inventive balloon catheter. The balloon catheter may be used in other processes. Other styles of embolus removing devices may be used in conjunction with the inventive balloon catheter, e.g., circular, proximal, or aspirating.

Of course, it should be apparent that this device and its clot removal ability may be used in other parts of the human body, e.g., in the periphery, the coronary, and the like. In addition, the balloon catheter may be used temporarily to occlude an artery for other diagnostic or therapeutic purposes, e.g., occluding an artery using vaso-occlusive devices or blocking bloodflow while introducing a medicine to a limited region of the vasculature.

The invention has been described and specific examples of the invention have been portrayed. The use of those specifics is not intended to limit the invention in any way. Additionally, to the extent that there are variations of the invention that are within the spirit of the disclosure and yet are equivalent to the inventions found in the claims, it is our intent that this patent cover those variations as well.

What is claimed is:

1. A catheter comprising;
   a catheter body comprising at least one polymeric tubular member; and
   a braided tubular structure comprising a plurality of component tubular members each having longitudinal lumens, woven radially in and out to form said braided tubular structure, wherein said braided tubular structure is embedded in a wall of the polymeric tubular member, wherein the component tubular members are comprised of metallic tubing.

2. The catheter of claim 1, where the metallic tubing comprises a superelastic alloy.

3. The catheter of claim 2, wherein the superelastic alloy comprises nickel and titanium.

4. A catheter comprising;
   a catheter body comprising at least one polymeric tubular member; and
   a braided tubular structure comprising a plurality of component tubular members each having longitudinal lumens, woven radially in and out to form said braided tubular structure, wherein said braided tubular structure is embedded in a wall of the polymeric tubular member, where said plurality of component tubular members longitudinal lumens are fluidly connected to a plenum at least one of the distal and proximal ends.

5. A catheter comprising;
   a catheter body comprising at least one polymeric tubular member; and
   a braided tubular structure comprising a plurality of component tubular members each having longitudinal lumens, woven radially in and out to form said braided tubular structure, wherein said braided tubular structure is embedded in a wall of the polymeric tubular member, further comprising a balloon on the catheter body connected to exchange inflation media through the lumens of the braided tubular structure.

* * * * *